United States Patent [19]

Radke

[11] Patent Number: 4,459,109

[45] Date of Patent: Jul. 10, 1984

[54] KINESIOGRAPH SENSOR ARRAY ALIGNMENT SYSTEM

[75] Inventor: John C. Radke, Seattle, Wash.

[73] Assignee: Myo-Tronics Research, Inc., Seattle, Wash.

[21] Appl. No.: 324,870

[22] Filed: Nov. 25, 1981

[51] Int. Cl.³ ............................................. A61C 19/04
[52] U.S. Cl. ...................................... 433/69; 128/777
[58] Field of Search ...................... 433/69, 68; 128/777

[56] References Cited

U.S. PATENT DOCUMENTS

| | | | |
|---|---|---|---|
| 3,390,459 | 7/1968 | Seidenberg | 433/69 |
| 3,983,865 | 10/1976 | Shepard | 128/777 |
| 4,197,855 | 4/1980 | Lewin | 128/777 |
| 4,303,077 | 12/1981 | Lewin et al. | 433/69 |
| 4,330,276 | 5/1982 | Becker et al. | 433/69 |
| 4,355,645 | 10/1982 | Mitani et al. | 128/777 |
| 4,383,535 | 5/1983 | Schorr | 128/777 |
| 4,386,405 | 5/1983 | Lewin et al. | 433/69 |
| 4,386,614 | 6/1983 | Ryan | 128/777 |

Primary Examiner—John J. Wilson
Attorney, Agent, or Firm—Seed and Berry

[57] ABSTRACT

A system for illuminating respective lamps to indicate the deviation from an optimum position of a kinesiograph sensor array in the anterior/posterior, vertical and lateral directions. The lamps are mounted on a panel in three sets of two corresponding to the three orthogonal axes. The panel is positioned on the chest of a patient during use so that it is in the same field of vision as the sensor array.

7 Claims, 3 Drawing Figures

KINESIOGRAPH SENSOR ARRAY ALIGNMENT SYSTEM

DESCRIPTION

1. Technical Field

This invention relates to dental diagnostic devices and, more particularly, to a system for properly positioning the sensor array of a kinesiograph.

2. Background Art

Dental diagnostic devices, known as kinesiographs, are used for displaying the movement of a patient's mandible on the screen of an oscilloscope. Basically, the kinesiograph includes an array of magnetic sensors which generate an output signal that is proportional to the distance between each sensor and a magnet affixed to the patient's mandible. The output signals from the sensors are applied to a display device which selects specific signals for display on a cathode ray tube as a function of either time or each other.

The kinesiograph measures the position of the mandible along three orthogonal axes. These axes are the anterior/posterior (A/P), the vertical (V) and the lateral (L). The position of the mandible along each axis is measured by a pair of sensors on opposite sides of the magnet. Consequently, the sensors are differential in nature with the signal at the output of one sensor increasing while the signal at the output of the other sensor is decreasing. The differential nature of the sensors results in a degradation in performance if the magnet is not positioned substantially midway between the sensors. This degradation primarily manifests itself as an output signal that is not a linear function of the position of the mandible, and this nonlinearity becomes more serious as the misalignment of the sensor array increases.

Kinesiograph sensor arrays have been heretofore aligned through a number of techniques. The initial alingnment technique is visual. The sensor array is positioned on the patient and it is adjusted until the sensors for each orthogonal axis appear to be equidistant from the magnet. This technique requires a surprisingly large amount of time, since the visual examination must be made in three planes. Furthermore, it is inherently inaccurate; and the degree of inaccuracy is not apparent nor is it measured.

The above-described limitations of the visual alignment technique have resulted in the development of an alignment technique utiliziling the cathode ray tube (CRT) display of the kinesiograph. This later technique results in a line extending from the center of the CRT screen in a direction indicative of the direction of misalignment, and the line has a length indicative of the magnitude of the misalignment. The advantage of this technique is that it provides a verification that the kinesiograph array is properly aligned before tests are made. However, it has three principal disadvantages. First, it is difficult to interpret the line since it often indicates a misalignment in two orthogonal directions. For example, a line extending at 45° at the center of the screen may indicate misalignment in the vertical and lateral axes. Correction of this misalignment requires that the sensor array be adjusted in both of these axes. Yet, it is generally recognized that positioning of objects is most advantageously accomplished by moving the object in one direction at a time without simultaneously moving it in any other direction. The second disadvantage of the CRT technique is that the line is only capable of indicating misalignments in two orthogonal planes at the same time. In order to align the sensor array in three orthogonal axes, two different combinations of sensor position outputs must be examined. The third disadvantage mentioned above arises from the CRT being positioned a considerable distance, and usually in a different direction, from the sensor array itself. As a result, the CRT and sensor array are not within the same field of view so that it is necessary for the practitioner to alternately look at the sensor array to make an adjustment and then to look at the CRT to determine if this adjustment was correct. This technique of alternately looking in two different directions markedly increases the time required to properly align a kinesiograph sensor array.

DISCLOSURE OF THE INVENTION

It is an object of the invention to provide a system for aligning a kinesiograph sensor array which provides a separate indication of misalignment for each orthogonal axes so that the indication may be easily interpreted.

It is another object of the invention to provide an alignment system for a kinesiograph sensor array having misalignment indicators which can easily be positioned in the field of view of the sensor array.

It is a further object of the invention to provide a kinesiograph sensor alignment system that can allow even inexperienced practitioners to quickly and easily align the array with an acceptable degree of accuracy.

These and other objects of the invention are provided by a system having a bi-directional comparison circuit for each orthogonal axis. The comparison circuit receives the position output for that axis and generates a first output signal when the position signal is larger than a first value and a second output signal when the position signal is smaller than a second value. The first value corresponds to a predetermined position deviation of the sensor array from an optimum position in one direction along the orthogonal axis while the second value corresponds to a deviation of the sensor array in the opposite direction. The outputs of the comparison circuits are applied to indicating means such as lamps which are actuated to identify the direction and axis along which the position of the sensor array deviates from the optimum position.

BEST MODE FOR CARRYING OUT THE INVENTION

Figure 1:
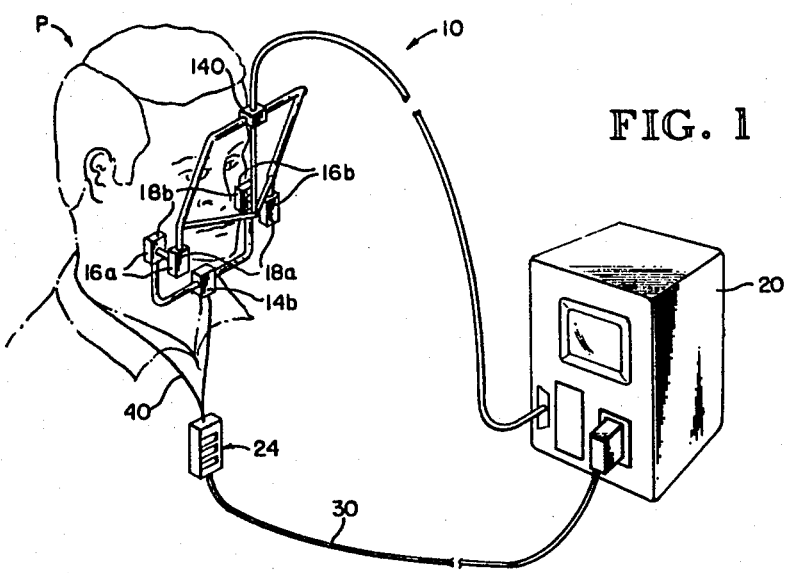
FIG. 1 is an isometric view illustrating the alignment system in operation with a conventional kinesiograph system.

A kinesiograph is used to examine the movement of the mandible of a patient P in the three orthogonal axes, namely, the anterior/posterior, lateral and vertical directions. The kinesiograph system 10 includes an array 12 of magnetic sensors 14,16,18 which generate respective output signals proportional to the distance between the sensor and a magnet M mounted on the mandible of the patient P. The sensors 14a,b are positioned above and below the magnet and are thus used to generate a position output indicative of the vertical position of the mandible. The sensors 16a,b are positioned on the left and right hand sides of the magnet M and are thus used to generate a position output indicative of the lateral position of the mandible. Finally, the sensors 18a,b are positioned in front of and behind the magnet M and are thus used to generate a position output indicative of the anterior/posterior position of the mandible.

The output signals from each sensor 14–18 are applied to a kinesiograph 20 which generates the position outputs from the sensor output signals and displays these signals either alone or in a combination selected by the operator. The kinesiograph 20 has an output jack 22 on which power and the anterior/posterior, vertical and lateral position outputs are present.

In operation, best results are achieved when the vertical sensors 14a,b are equally positioned above and below the magnet M, the lateral sensors 16a,b are positioned equally to the left and right of the magnet M and the sensors 18a,b are equally positioned above and behind the magnet M.

Figure 2:
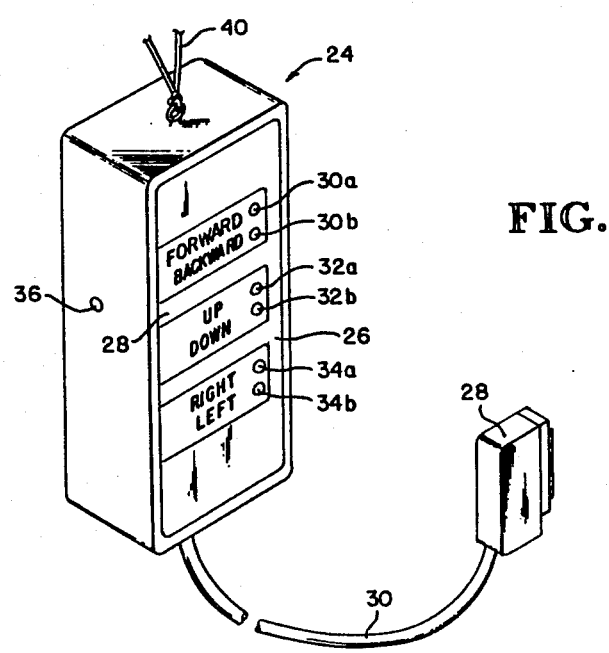
FIG. 2 is an isometric view of the alignment system.

The kinesiograph alignment system, illustrated in greater detail in FIG. 2, provides easily interpreted indications identifying the direction of misalignment and commanding the direction of movement to correct the misalignment. The alignment system 24 includes an enclosure 26 which is connected to a conventional plug 28 through a multiconductor cable 30. The plug 28 is inserted into jack 22 of the kinesiograph device 20 as explained above. The face of the enclosure 26 includes a panel containing three sets of lamps 30,32,34. Each set of lamps 30,32,34 corresponds to one axis of alignment. The lamps 30a–34b indicate the direction that the sensor array should be moved to correct for the misalignment. Thus, illumination of lamp 30a indicates that the sensor array should be moved forwardly along the anterior-posterior axis. Lamp 30b indicates that the array 12 should be moved rearwardly. Similarly, illumination of lamp 32a indicates that the sensor should be moved up along the vertical axis. Lamp 32b indicates that the sensor array 12 should be moved downwardly. Finally, illumination of lamp 34a indicates that the sensor array 12 should be moved to the left along the lateral axis. Lamp 34b indicates that the sensor array 12 should be moved to the left.

One side of the enclosure 26 contains a circular aperture 36 which provides access to a potentiometer (explained hereinafter) which controls the degree of misalignment that causes the lamps 30a–34b to become illuminated. Thus, once a given alignment requirement is set, the practitioner need not be concerned with where in that range the sensor array 12 is positioned. This markedly expedites the alignment process. Moreover, each lamp provides an indication of a misalignment in a single direction along an axis so that correction can be accomplished by simply moving the sensor array 12 in that direction. Correction of a misalignment thus does not require simultaneous movement of the array 12 in more than one direction.

Turning now to FIG. 1, the alignment system 24 is preferably mounted on the chest of the patient P by a chain 40 or similar structure so that the lamps 30a–34b are in the field of view of the practitioner who is adjusting the sensor array 12. Thus it is not necessary for the practitioner to alternately look at the array to make an adjustment and then look at an indicating device to determine if the adjustment is correct. This property also greatly expedites the alignment procedure.

Figure 3:
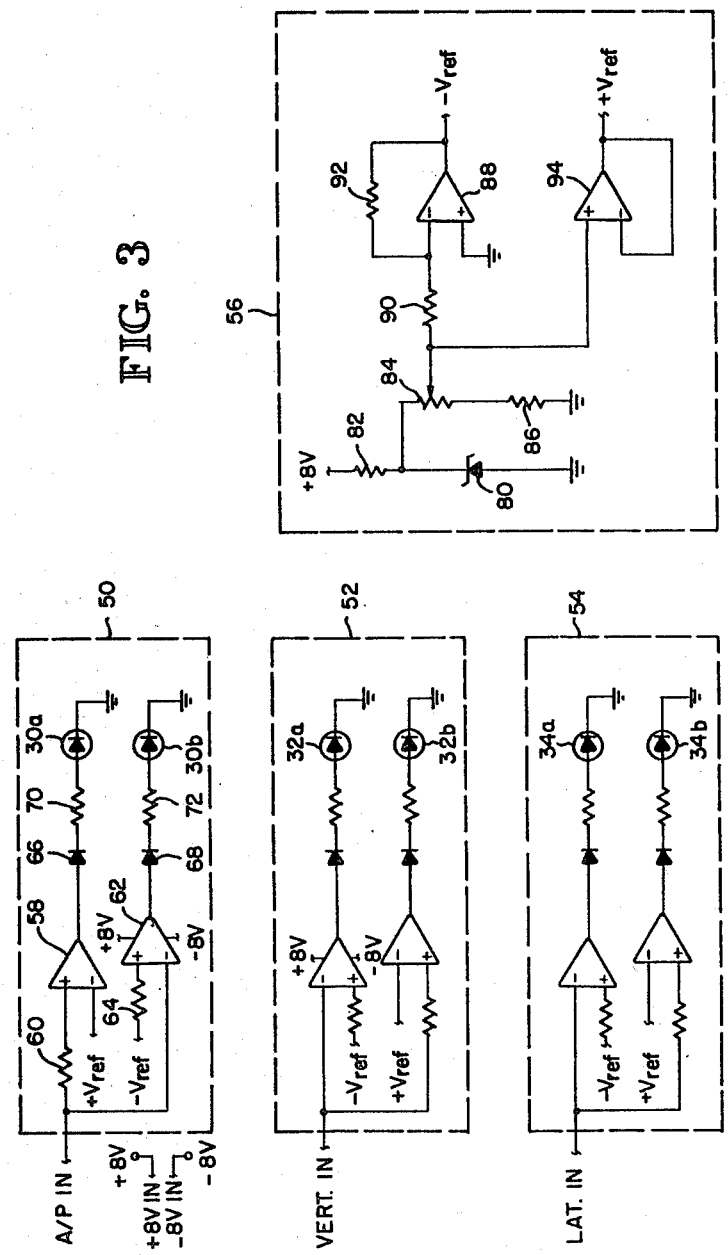
FIG. 3 is a schematic of the circuitry for the alignment system.

A schematic of the alignment system is illustrated in FIG. 3. Basically, the alignment system includes three identical bi-lateral comparison circuits 50,52,54 and a reference signal generator 56. The comparison circuit 50 receives the anterior/posterior position output from the kinesiograph 20, the comparison circuit 52 receives the vertical position output and the comparison circuit 54 receives the lateral position output. Insofar as the comparison circuits 50–54 are substantially identical, only the operation of comparison circuit 50 is explained in detail herein.

The position output is applied to the positive input of a comparator 58 through resistor 60 and directly to the negative input of a second comparator 62. The negative input of comparator 58 receives a positive reference signal $+V_{ref}$, while the positive input to comparator 62 receives a a negative reference signal $-V_{ref}$ through resistor 64. The positive and negative reference signals preferably have the same magnitude although different polarities. In operation, the comparators 58,62 generate a positive output when the signal applied to their positive input has a magnitude greater than the signal applied to their negative inputs. Conversely, the comparators 58,62 generate negative outputs when the signal applied to their negative inputs have a magnitude that is greater than the magnitude of the signal applied to their positive inputs. The outputs of the comparators 58,62 are applied to their respective light-emitting diodes 30a,30b through respective diodes 66,68 and resistors 70,72. The diodes 66,68 prevent the light-emitting diodes 30a,30b from being back-biased responsive to a negative output from comparators 58,62 while the resistors 70,72 limit the current flow through the light-emitting diodes 30a,30b.

The reference signals $+V_{ref}$ and $-V_{ref}$ are produced by the reference generator circuit 56. The positive supply voltage is applied to a zener diode 80 through resistor 82. The stable positive voltage across zener diode 80 is applied to a series combination of potentiometer 84 and resistor 86. The wiper of potentiometer 84 is applied to an operational amplifier 88 through a resistor 90. A feedback resistor 92 sets the gain of the amplifier 88 at unity. As a result, the negative reference signal $-V_{ref}$ is a negative voltage having a magnitude equal to the voltage on potentiometer 84. This voltage is also applied to a voltage follower operational amplifier 94 to generate the positive reference signal $+V_{ref}$.

In operation, misalignment of the sensor array 12 in the rearward direction causes the kinesiograph 20 to generate a positive anterior-posterior position output. As the misalignment increases, the magnitude of the voltage exceeds the positive reference signal $+V_{ref}$, thereby causing the comparator 58 to generate a positive output which illuminates light-emitting diode 30a to generate a forward command. Similarly, a forward misalingment of the sensor array 12 causes the kinesiograph 20 to generate a negative anterior/posterior position output which, as the misalignment increases, eventually becomes more negative than the negative reference signal $-V_{ref}$. Comparator 62 then generates a positive output which illuminates light-emitting diode 30b to provide a rearward movement command. The magnitude of the reference signals $+V_{ref}$ and $-V_{ref}$ may be adjusted by adjusting the position of the wiper of potentiometer 84 through aperture 36 in order to ensure any desired degree of alignment.

The kinesiograph alignment system thus allows quick and easy alignment of a kinesiograph sensor array by even inexperienced or unskilled personnel.

I claim:

1. A system for facilitating the alignment of an array of kinesiograph sensors, comprising:
   a kinesiograph having an array of sensors, said kinesiograph generating respective position outputs indicative of the position of said array with respect to a patient's mandible along at least two orthogonal axes;
   bidirectional comparison means for each of said position outputs, each of said comparison means generating a first output signal responsive to its corresponding position signal being larger than a first value representing a predetermined deviation of said sensor array from an optimum position in one direction along the corresponding orthogonal axis, said comparison means generating a second output signal responsive to its corresponding position signal being smaller than a second value representing a predetermined deviation of said sensor array from said optimum position in the opposite direction along the corresponding orthogonal axis; and
   indicating means for each output signal of each bidirectional comparison means, each of said indicating means being actuated by its respective output signal to identify the direction and axis along which the position of said sensor deviates from said optimum position, thereby allowing the position of said sensor array to be adjusted until none of said indicating means is actuated.

2. The system of claim 1 wherein each of said bidirectional comparison means comprise first and second comparator circuits each having positive and negative input terminals and an output terminal on which is generated a signal of a first magnitude when the magnitude of the signal applied to the positive input terminal is greater than the signal applied to the negative input terminal and a signal of a second magnitude when the magnitude of the signal applied to the positive input terminal is less than the signal applied to the negative input terminal, each position output being applied to the positive input terminal of said first comparator circuit and to the negative input terminal of said second comparator circuit, said comparison means further including a reference signal generator applying a first reference signal to the negative input terminal of said first comparator circuit and a second reference signal to the positive input terminal of said second comparator circuit, the output terminal of each comparator circuit being connected to respective indicating means which are actuated by a signal on said output terminal whereby said first comparator circuit actuates its corresponding indicating means when the position output applied to its positive input terminal has a magnitude that is larger than said first reference signal and said second comparator circuit actuates its corresponding indicating means when the position output applied to its negative input terminal has a magnitude that is smaller than said second reference signal.

3. The alignment system of claim 1 wherein said indicating means comprise a pair of indicating lamps connected to each bi-directional comparison means and receiving in respective first and second output signals thereof to identify the direction and orthogonal axis of said deviation.

4. The alignment system of claim 3 wherein bi-directional comparison means are provided for the anterior/posterior, lateral and vertical axes of said kinesiograph sensor array and said indicating lamps are arranged on a common panel in three sets of two corresponding to each direction of said axes, said panel including mounting means for positioning said panel on the chest of said patient so that said indicating lamps and said sensor array are positioned in the same field of view.

5. The alignment system of claim 4 wherein each of said indicating lamps are labeled with an indication of the direction that said sensor array should be moved to place it in the optimum position.

6. A system for facilitating an alignment of an array of kinesiograph sensors, comprising:
   a kinesiograph having an array of sensors, said kinesiograph generating respective position outputs indicative of the position of said array with respect to a patient's qandible and the anterior/posterior, vertical and lateral directions, said systems comprising:
   a reference circuit generating a first reference signal of one magnitude and a second reference signal of another magnitude;
   a first anterior/posterior comparator circuit receiving said anterior/posterior position output and said first reference signal, said comparator circuit generating an actuating signal at its output when said sensor array is positioned forward of an optimum position by a predetermined value corresponding to said first reference signal;
   a second anterior/posterior comparator circuit receiving said anterior/posterior output and said second reference signal, said comparator circuit generating an actuating signal at its output when said sensor array is positioned behind an optimum position by a predetermined value corresponding to said second reference signal;
   a first vertical comparator circuit receiving said vertical position output and said first reference signal, said comparator circuit generating an actuating signal at its output when said sensor array is positioned above an optimum position by a predetermined value corresponding to said first reference signal;
   a second vertical comparator circuit receiving said vertical position output and said second reference signal, said comparator circuit generating an actuating signal at its output when said sensor array is positioned below an optimum position by a predetermined value corresponding to said second reference signal;
   a first lateral comparator circuit receiving said lateral position output and said first reference signal, said comparator circuit generating an actuating signal at its output when said sensor array is positioned to the right of an optimum position by a predetermined value corresponding to said first reference signal;
   a second lateral comparator circuit receiving said lateral position output and said second reference signal, said comparator circuit generating an actuating signal at its output when said sensor array is positioned to the left of an optimum position by a predetermined value corresponding to said second reference signal; and
   an indicator connected to the output of each comparator circuit lamps are illuminated upon receipt of respective actuating, said indicator identifying the direction and axis of the position deviations of said sensor array.

7. The system of claim 6 wherein each of said indicating lamps are labeled with an indication of the direction that said sensor array should be moved to place it in the optimum position.

* * * * *